US012742385B2

(12) United States Patent
Maity et al.

(10) Patent No.: US 12,742,385 B2
(45) Date of Patent: Sep. 22, 2026

(54) METHOD FOR PROCESSING SAMPLED PROPPANT DURING HYDRAULIC FRACTURING

(71) Applicant: GTI ENERGY, Des Plaines, IL (US)

(72) Inventors: Debotyam Maity, Elk Grove Village, IL (US); Jordan Ciezobka, Addison, IL (US)

(73) Assignee: GTI ENERGY, Des Plaines, IL (US)

(*) Notice: Subject to any disclaimer, the term of this patent is extended or adjusted under 35 U.S.C. 154(b) by 722 days.

(21) Appl. No.: 17/969,393

(22) Filed: Oct. 19, 2022

(65) Prior Publication Data

US 2023/0123954 A1 Apr. 20, 2023

Related U.S. Application Data

(60) Provisional application No. 63/257,858, filed on Oct. 20, 2021.

(51) Int. Cl.
*E21B 49/00* (2006.01)
*C09K 8/80* (2006.01)
(Continued)

(52) U.S. Cl.
CPC .............. *E21B 49/005* (2013.01); *C09K 8/80* (2013.01); *G01N 23/2251* (2013.01);
(Continued)

(58) Field of Classification Search
CPC ........ E21B 49/00; E21B 49/005; E21B 49/06; E21B 49/08; E21B 49/087; E21B 49/0875; E21B 49/088; E21B 49/10; E21B 47/10; E21B 43/267; E21B 47/135; C09K 8/80; G01N 23/2251; G01N 33/2823; G01N 2001/1025; G01N 2223/616; G01N 2223/635; G01N 2223/40;
(Continued)

(56) References Cited

U.S. PATENT DOCUMENTS 11,492,900 B2 * 11/2022 Wright .................. E21B 49/005
2002/0118406 A1 8/2002 Huang
(Continued)

OTHER PUBLICATIONS

Maity et al., "Assessment of In-Situ Proppant Placement in SRV Using Through-Fracture Core Sampling at HFTS." Paper presented at the SPE/AAPG/SEG Unconventional Resources Technology Conference, Houston, Texas, USA, Jul. 2018. (Year: 2018).*
(Continued)

*Primary Examiner* — Andrew Schechter
*Assistant Examiner* — Matthew W. Baca
(74) *Attorney, Agent, or Firm* — Pauley Erickson & Swanson

(57) ABSTRACT

A method for processing proppant from a well. A plurality of proppant samples are collected during drilling of a well for imaging analysis. In addition to imaging analysis a further correction factor is determined for the samples using additional analysis on a portion of the samples. Determining and applying the correction factor to the imaging results provides a more accurate proppant log. The additional analysis can be by scanning electron microscopy, such as for differentiating the silicon proppant particles from other elemental particles resulting from the drilling.

18 Claims, 13 Drawing Sheets

(51) Int. Cl.

| | |
|---|---|
| ***G01N 23/2251*** | (2018.01) |
| ***G01N 33/28*** | (2006.01) |
| *E21B 43/267* | (2006.01) |
| *G01N 1/10* | (2006.01) |

(52) U.S. Cl.

CPC ........ *G01N 33/2823* (2013.01); *E21B 43/267* (2013.01); *G01N 2001/1025* (2013.01); *G01N 2223/616* (2013.01)

(58) Field of Classification Search

CPC ............. G01N 2223/418; G01N 15/00; G01N 15/0227; G01N 15/02

See application file for complete search history.

(56) References Cited

U.S. PATENT DOCUMENTS

| | | | | |
|---|---|---|---|---|
| 2008/0210421 | A1 | 9/2008 | Wilson et al. | |
| 2010/0313645 | A1 | 12/2010 | Doman et al. | |
| 2014/0014348 | A1 | 1/2014 | Mahoney et al. | |
| 2014/0182841 | A1 | 7/2014 | Lecerf et al. | |
| 2016/0283651 | A1 | 9/2016 | Knight et al. | |
| 2018/0223641 | A1* | 8/2018 | Ciezobka | G01N 15/0227 |
| 2021/0332700 | A1* | 10/2021 | Pelletier | E21B 49/081 |

OTHER PUBLICATIONS

King, George, "Utilizing Fluid & Proppant Tracer Results to Analyze Multi-Fractured Well Flow Back in Shales: A Framework for Optimizing Fracture Design and Application," SPE Hydraulic Fracturing Technology Conference, Paper No. SPE-140105, Jan. 24, 2011 (19 pages).

Palisch, T., "Far-Field Proppant Detection Using Electromagnetic Methods-Latest Field Results," SPE Hydraulic Fracturing Technology Conference and Exhibition, No. SPE-184880-MS, Jan. 24, 2017, (16 pages).

PCT International Search Report, Form PCT/ISA/210, for International Application PCT/US2022/47216, Oct. 20, 2022 (5 pages).

PCT Written Opinion of International Searching Authority, Form PCT/ISA/237, for International Application PCT/US2022/47216, Oct. 20, 2022 (6 pages).

Maity et al. "A Systematic Interpretation of Subsurface Proppant Concentration from Drilling Mud Returns: Case Study from Hydraulic Fracturing Test Site in Delaware Basin," Unconventional Resources Technology Conference in Houston TX, Jul. 26-28, 2021, URL:https://www.osti.gov/servlets/purl/1855735, Feb. 22, 2023, (13 pages).

Maity et al. "Assessment of In-situ Proppant Placement in SRV Using Through-Fracture Core Sampling at HETS" Unconventional Resources Technology Conference, Jul. 23-25, 2018, URL:https://onepetro.org/URTECONF/proceedings-abstract/1BURTC/2-1BURTC/D023S023R004/156978, Feb. 22, 2023, (16 pages).

https://carboceramics.com/products/proppant-technologies/fracture-evaluation, Evaluate Perforation Cluster Efficiency & Near-Wellbore Connectivity.

https://doi.org/10.1016/j.petrol.2020.107048, Zhao Bochao, "Tracer cluting proppants for hydraulic fracture characterization" Hildebrand Department of Petroleum & Geosystems Engineering, University of Texas, Journal of Petroleum Science and Engineering, 0920-4105/© 2020 Elsevier B.V., Feb. 13, 2020, (9 pages).

https://doi.org/10.2118/140105-MS, King E.George, Utilizing Fluid & Proppant Tracer Results to Analyze Multi-Fractured Well Flow Back in Shales: A Framework for Optimizing Fracture Design and Application, Paper presented at the SPE Hydraulic Fracturing Technology Conference, Woodlands, Texas, Paper No. SPE-140105-MS, Published Jan. 24, 2011 (1 page).

https://doi.org/10.2118/184880-MS, Palisch .T, "Far-Field Proppant Detection Using Electromagnetic Methods-Latest Field Results," Paper presented at SPE Hydraulic Fracturing Technology Conference and Exhibition, No. SPE-184880-MS, Woodlands, Texas, Jan. 24, 2017, (2 Pages).

* cited by examiner

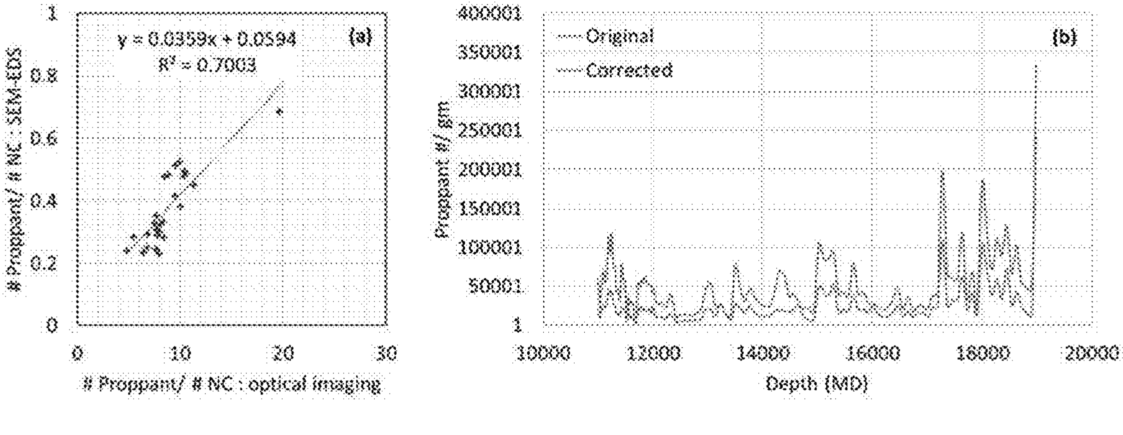
FIG. 5A
FIG. 5B
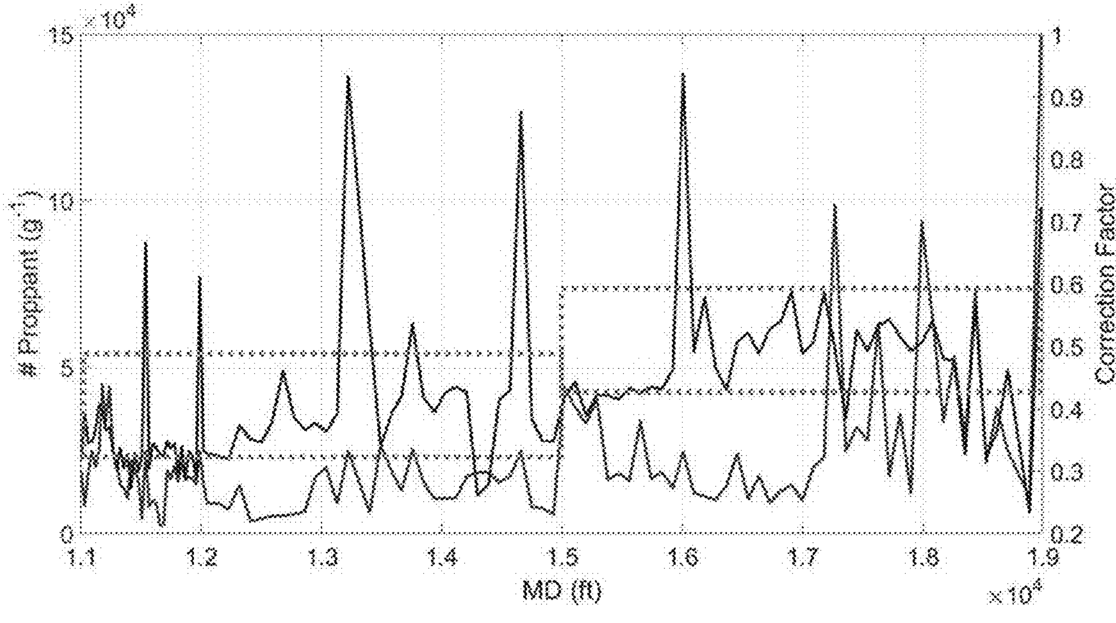
FIG. 6

METHOD FOR PROCESSING SAMPLED PROPPANT DURING HYDRAULIC FRACTURING

CROSS REFERENCE TO RELATED APPLICATION

This application claims the benefit of U.S. Provisional Patent Application Ser. No. 63/257,858, filed on 20 Oct. 2021. The provisional application is hereby incorporated by reference herein in its entirety and is made a part hereof, including but not limited to those portions which specifically appear hereinafter.

STATEMENT REGARDING FEDERALLY SPONSORED RESEARCH

This invention was made with government support under Award Numbers DE-FE0031577 and DE-FE0024292, awarded by the Department of Energy. The government has certain rights in the invention.

BACKGROUND OF THE INVENTION

Field of the Invention

This invention relates generally to sampling proppant and, more particularly, to a process to validate imaging results of proppant for accurate analysis.

Description of Prior Art

Proppant is a particulate material suspended in water or another fluid often used in hydraulic fracturing.

Prior systems determine baseline proppant results from an imaging workflow. Results obtained by such workflow through imaging analysis can be impacted by a variety of factors. Such factors include factors intrinsic to the rock and the drilling/coring process, such as rocks being drilled through, varying rates of penetration, mud system, etc., as well as factors associated with imaging workflow, particularly during sample preparation. Depending on variations in cleaning processes such as subjective biases, it is not very reliable to use only proppant imaging results to determine proppant analysis. Therefore, improved techniques to analyze proppant samples are desired.

SUMMARY OF THE INVENTION

The invention generally relates to a more accurate analysis of sampled proppant. The general object of the invention can be attained, at least in part, through a process to validate imaging results of proppant for an accurate analysis.

The ratio of proppant to other minerals in samples which show proppant-like characteristics often gives a very strong indicator of "presence" of proppant in samples via imaging analysis. Proppant-like characteristics can refer to optical properties such as translucence, hue, and circularity, among others. Relative proppant presence in samples is agnostic of imaging workflow subjectivities. For example, use of higher or lower thresholds for particle classification and varying degrees of clean-up can result in varying results from object detection and classification workflow. This is because the workflow uses several particle image attributes which are impacted by the subjectivities.

However, samples with high proppant counts will still show elevated proppant values in these results even though the relative abundance of particles may vary. A representative sample or multiple representative proppant samples can be analyzed for their elemental composition and relative presence of proppant or other mineral particles can be accurately identified. Observed results can then be corrected for the original sample imaging using a correction factor identified from the analysis. For example, using scanning electron microscopy (SEM) in accordance with the subject invention for elemental composition analysis, on selected samples, can provide enough data to allow for an accurate relative proppant indication which can then be applied on a full proppant dataset to more accurately determine final proppant counts.

The invention includes a method for processing proppant from a well. The method including the steps of: collecting a plurality of proppant samples during drilling of a well; obtaining imaging results from the plurality of proppant samples collected; determining a correction factor from a sample subset of the plurality of proppant samples; and applying the correction factor to the imaging results to obtain corrected proppant data. The correction factor is desirably determined by elemental analysis (e.g., SEM) of the sample subset. The subset samples can be collected, for example, by collecting the sample subset at one of a mud and cuttings inlet, a liquids and fine solids discharge, and/or a cuttings discharge of a mud/drill cuttings handling system, such as a cleaner, shale shaker, or other equivalent equipment.

In embodiments of this invention, the correction factor is a correction curve. In additional or alternative embodiments, the correction factor is or is based upon an element ratio of silicon (Si) (i.e., the proppant) to calcium (Ca) and/or barium (Ba) in the subset of the plurality of proppant samples. The correction factor is used to adjust an imaging element ratio in the imaging results as a function of the element ratio of the correction factor.

In embodiments of this invention, the subset samples are taken for, or otherwise used to determine a particular zone of a distance range within the well. Once the distance zone is determined, the correction factor for the corresponding zone can be applied to all proppant samples taken within the zone.

In other embodiments of this invention, the correction factor is normalized as a function of a rate of drilling or penetration at a time of the sample collection.

The invention further includes a method for processing proppant from a well, including the steps of: collecting a plurality of proppant samples during drilling of a well; obtaining imaging results from the plurality of proppant samples collected; determining proppant values in the plurality of proppant samples using a SEM analysis; generating a correction factor from the SEM analysis; and validating or updating/correcting the imaging results with the correction factor. The method desirably further includes applying the correction factor to proppant log data, and producing a corrected proppant log.

Optimal spacing between horizontal wells is required for hydraulic fracturing. The subject invention seeks to determine and/or minimize fracture driven interactions or well interference. Proppant log techniques according to the subject invention aid with proper identification.

In embodiments, the information provided by the subset samples can further be used to understand the fractures within the well. In embodiments, the method includes determining a number of proppant particles in the subset sample within each of a plurality of particle size ranges, which is then used to interpret the hydraulic fractures as a function of a particle size distribution within the sample subset. The particle size can additionally or alternatively be used to identify a source of the proppant within the sample, such as if the fracturing from adjacent wells interconnects.

Other objects and advantages will be apparent to those skilled in the art from the following detailed description taken in conjunction with the appended claims and drawings.

BRIEF DESCRIPTION OF THE DRAWINGS

FIG. 3 shows SEM-EDS composition maps for identifying proppant ratios according to one embodiment of this invention.

FIG. 4 shows subsurface proppant particles according to embodiments of this invention.

FIGS. 5A and 5B shows a correction plot derived from SEM-EDS analysis before and after correction of proppant log data according to one embodiment of this invention.

FIG. 6 shows a graphical representation of correction factors identified at various depths according to one embodiment of this invention.

DETAILED DESCRIPTION OF THE INVENTION

Figure 2:
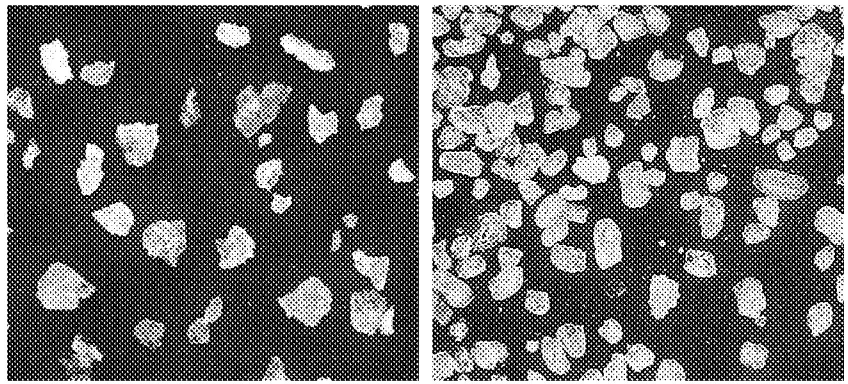
FIG. 2 shows calcite and proppant particles according to one embodiment of this invention.

The present invention provides a process for accurately determining proppant particles. Proppant particles, and other minerals with similar optical properties, tend to be hard to distinguish using traditional imaging workflows. This is particularly true for particles with smaller size ranges (approximately 50 μm to 120 μm). FIG. 2 shows examples of proppant and calcite cement particles at these small size ranges obtained by controlled sampling. Downhole samples are more difficult to distinguish by imaging as these particles undergo abrasive action from fluid movement.

Figure 1:
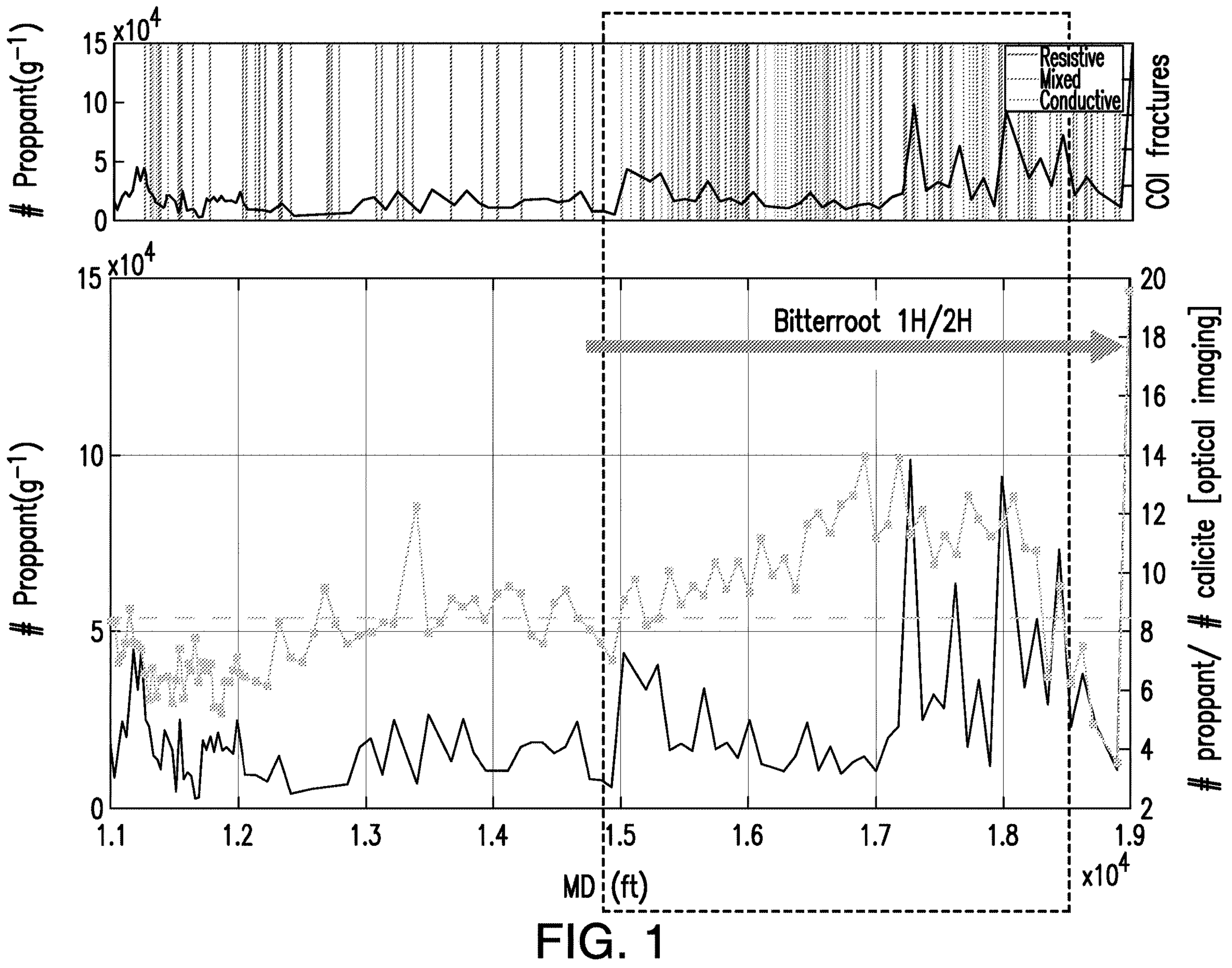
FIG. 1 shows a graphical representation of interpreted hydraulic fractures compared with observed proppant to mineral ratios according to one embodiment of this invention.

Baseline proppant results are available from an imaging workflow. The claimed invention incorporates an additional analysis step using scanning electron microscopy (SEM) analysis of samples that have already been imaged. Using SEM-EDS in accordance with the subject invention for elemental composition analysis, on selected samples, can provide enough data to allow for an accurate relative proppant indication which can then be applied on a dataset to more accurately determine final proppant counts, as shown in FIG. 1. A representative sample or multiple representative samples can be analyzed for their elemental composition and relative presence of proppant or other mineral particles can be accurately identified. Observed results can then be corrected for the original sample imaging using a correction factor identified from the SEM analysis.

SEM analysis allows for an understanding of the chemical composition of the samples. Proppant particles are rich in Si whereas other, different minerals such as sulphates or calcites do not show significant Si but are instead usually rich in Ca or Ba. Other particles, such as shales, are richer in Al, Mg, etc. With known chemical compositions of samples of interest, proppant particles can be isolated from other particles that may show proppant-like characteristics.

Most samples show natural minerals to be either calcites or sulphates ($CaCO_3$/$BaSO_4$). Embodiments of the invention utilizes relative compositions of Si rich vs. Ca or Ba rich samples. Once these ratios are identified from the SEM analysis, they can be compared with observed ratios from the original imaging workflow to figure out how much correction may be necessary in the data. A relatively small amount of material is used to prepare samples to be imaged and analyzed for a bench scale SEM-EDS system.

FIG. 3 shows two samples that contain varying quantities of proppant.

FIG. 4 shows another set of examples containing varying levels of proppant from negligible proppant particles to significant proppant and calcite or other mineral particles. Proppant ratios of the samples can be compared with ratios observed from original imaging analysis. Output or corrected (SEM derived) ratios can then be modeled using regression analysis.

FIG. 5 shows imaging vs. SEM ratios and a regression model that can be used for corrections. FIG. 5 shows 223 samples collected with 23 points per sample selected for SEM based QC (quality control). The corrected data vs. the original data is also shown in FIG. 5.

While the impact on individual samples in terms of corrections can be significant, an overall trend maintains the behavior in the proppant distribution data. FIG. 6 shows higher correction factors identified from samples above 15,000 feet on average, compared to samples taken at shallower depths. This corresponds to the depth at which hydraulic fractures begin showing in FIG. 1.

Figure 7:
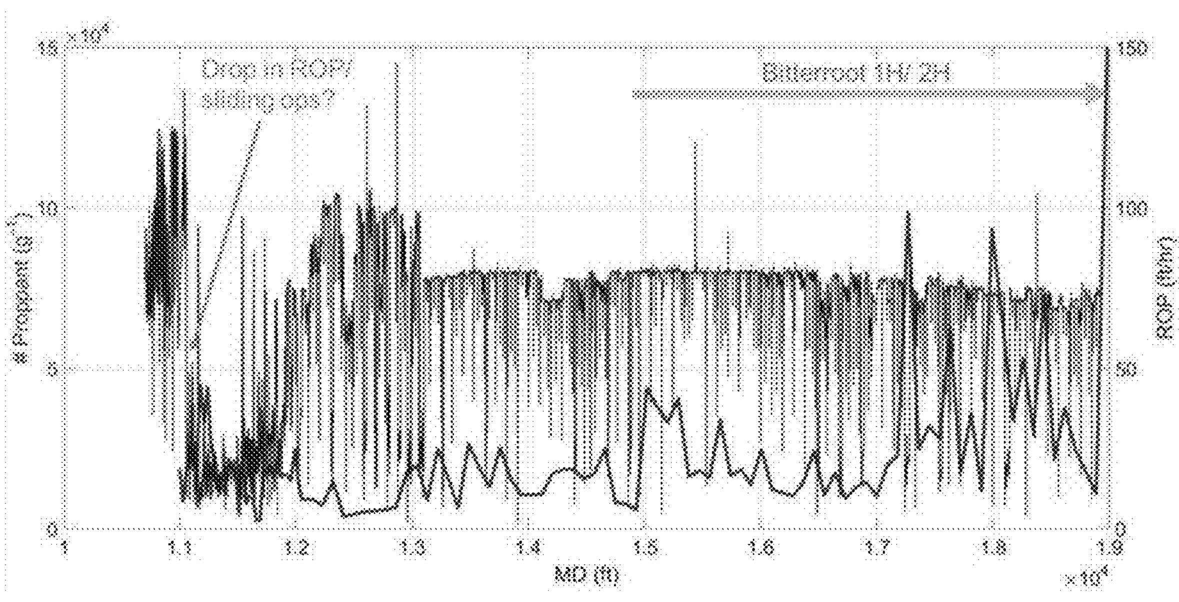
FIG. 7 shows a graphical representation of penetration behavior compared with proppant counts according to one embodiment of this invention.

Another important aspect considered in the subject invention is curve normalization based on varying rates of drilling or penetration (ROP). FIG. 7 shows ROP normalization for in-fill drilling cases. More particularly, FIG. 7 shows ROP behavior across lateral compared with proppant counts. Varying ROP on final proppant logs can have a detrimental impact to the results. Specifically, at lower ROP's, particle counts tend to be higher due to more re-circulation over a given period. At higher ROP's, the amount of material being re-circulated is relatively lower. Therefore, it is important to maintain a consistent ROP over a logged length and if not, data normalization is necessary to recover a more accurate proppant distribution. FIG. 7 shows the impact of a drop in ROP as a lateral was built during the transition from vertical to near horizontal drilling. Without correction, the proppant distribution from the log may only be useful or comparable from a depth of 13000 ft. MD onwards. There are also ways to normalize for changing ROP. For example, a median filtered ROP curve can be generated to remove outliers. Then, medium adjusted ROP values are computed. Since most of the ROP data is stabilized at approximately 75 ft/hour to 80 ft/hour, the normalized distribution weighs lower ROP's lower and weighs ROP's close to the median at approximately 1. This can then be used as a multiplier for the proppant data and can retain most of the data past 13000 ft. MD, as is, and reduce the values prior to 12000 ft. MD.

When it comes to normalization for proppant screen-out conditions, proppant distribution, particularly at very high sampling rates (such as one sample every 3 to 6 feet, for example), the impact of individual fracture morphologies and consequent localized screen-out can be significant. At lower sampling rates (such as 10's of feet per sample, for example) surface sample collection allows for moderation, however subsurface samples need to be further normalized to reduce the impact of localized screen-out behavior.

Figure 8:
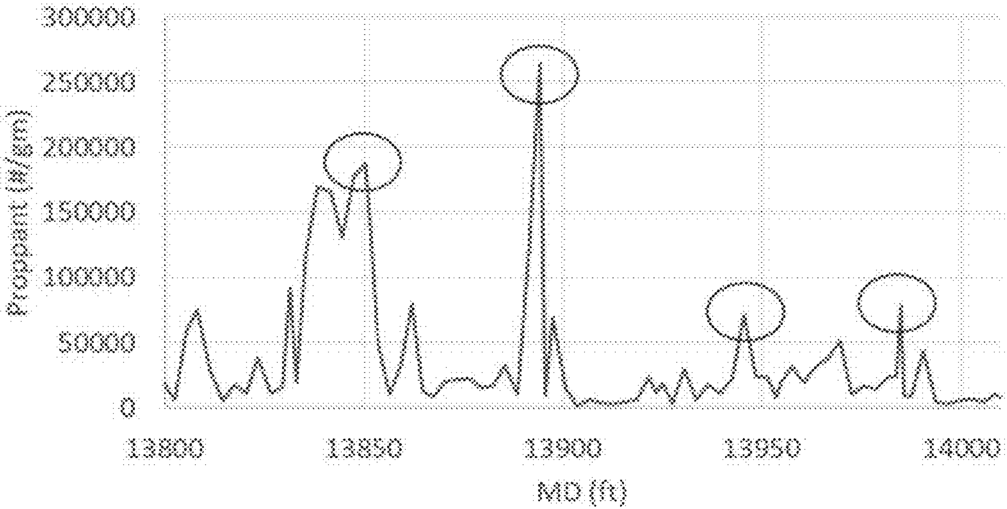
FIG. 8 shows a graphical representation of proppant distribution from a cored interval according to one embodiment of this invention.

FIG. 8 shows distribution from samples collected from a core. Here, the sampling rate was every 3 feet. At the high resolution shown in FIG. 8, localized peaks are shown in the distribution as a result of fracture morphologies and complexities associated with bed boundaries and high stress contrast zones.

There are various approaches to normalization available. Often very high proppant peaks are associated with localized screen-out and therefore, these high peaks are likely not well drained. However, higher ratios of proppant particles to other minerals are a good indicator of propped fractures. Therefore, normalization according to the subject invention can occur by maximizing the ratio and minimizing maximum proppant identified at sampling locations.

Figure 9A:
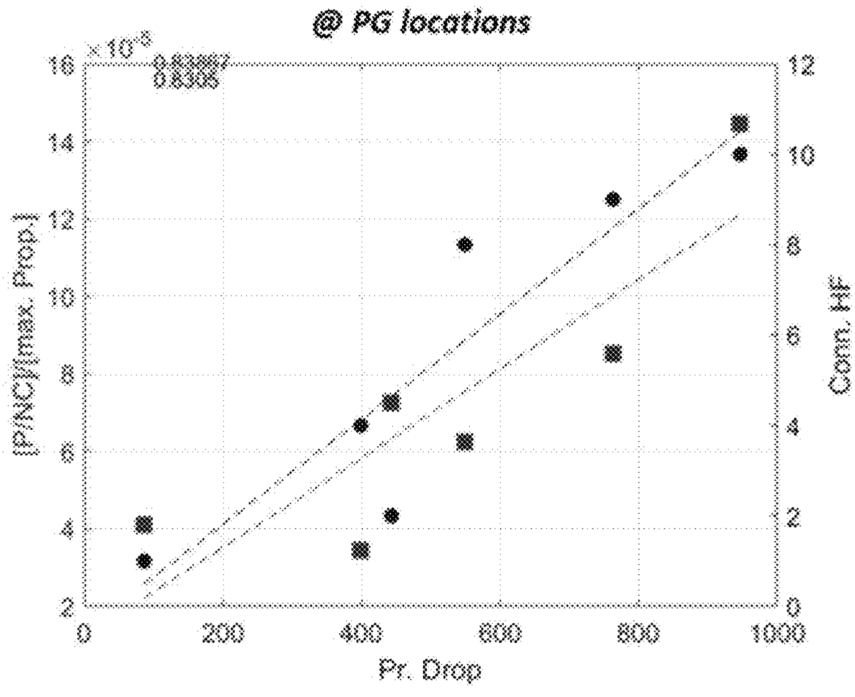
FIGS. 9A and 9B show graphical representations of normalization results to remove an impact of proppant outliers according to one embodiment of this invention.
Figure 9B:
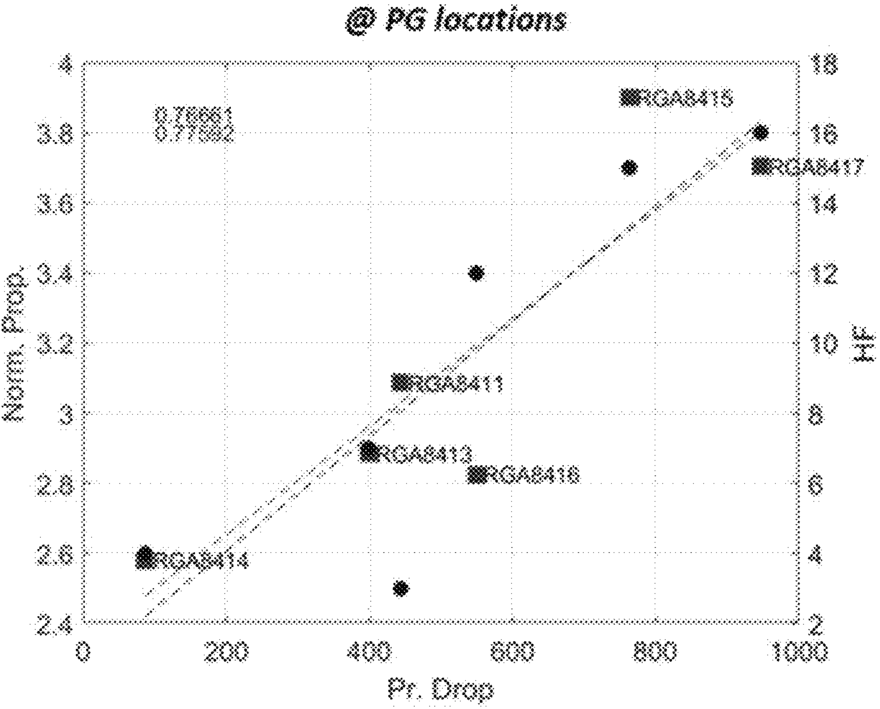

FIG. 9 shows two normalization results according to the present invention to remove an impact of proppant screen-out outliers and compare those results with hydraulic fractures. In this example, results were observed to drainage behavior at various locations in cored wells. Pressure gauges were placed in the cored wells at specific depths of interest and then the pressure was monitored over a period of a few years to see how pressure drawdown varied over time. The drawdown behavior was found to be strongly correlated with proppant as well as hydraulic fractures. The normalized parameter shared here as well as other methods have shown a strong correlation with the fractures and drawdown behavior as seen in FIG. 9.

Several normalization approaches were used in the examples shown in FIG. 9. The normalization relationship can be shown by the following equations, for example.

$$\text{Normalization of Proppant} = fx\left[\frac{\dfrac{\#\mathrm{P}_i}{\sum_{i-win}^{i+win}\#\mathrm{P}_i}}{2\times\mathrm{win}}\right]$$

$$\text{Normalization of Proppant} = fx\left[\frac{\sum_{i-win}^{i+win\#\mathrm{P}_i}/\#\mathrm{NC}_i}{\max\limits_{i-win:i+win} P_i}\right]$$

Figure 10:
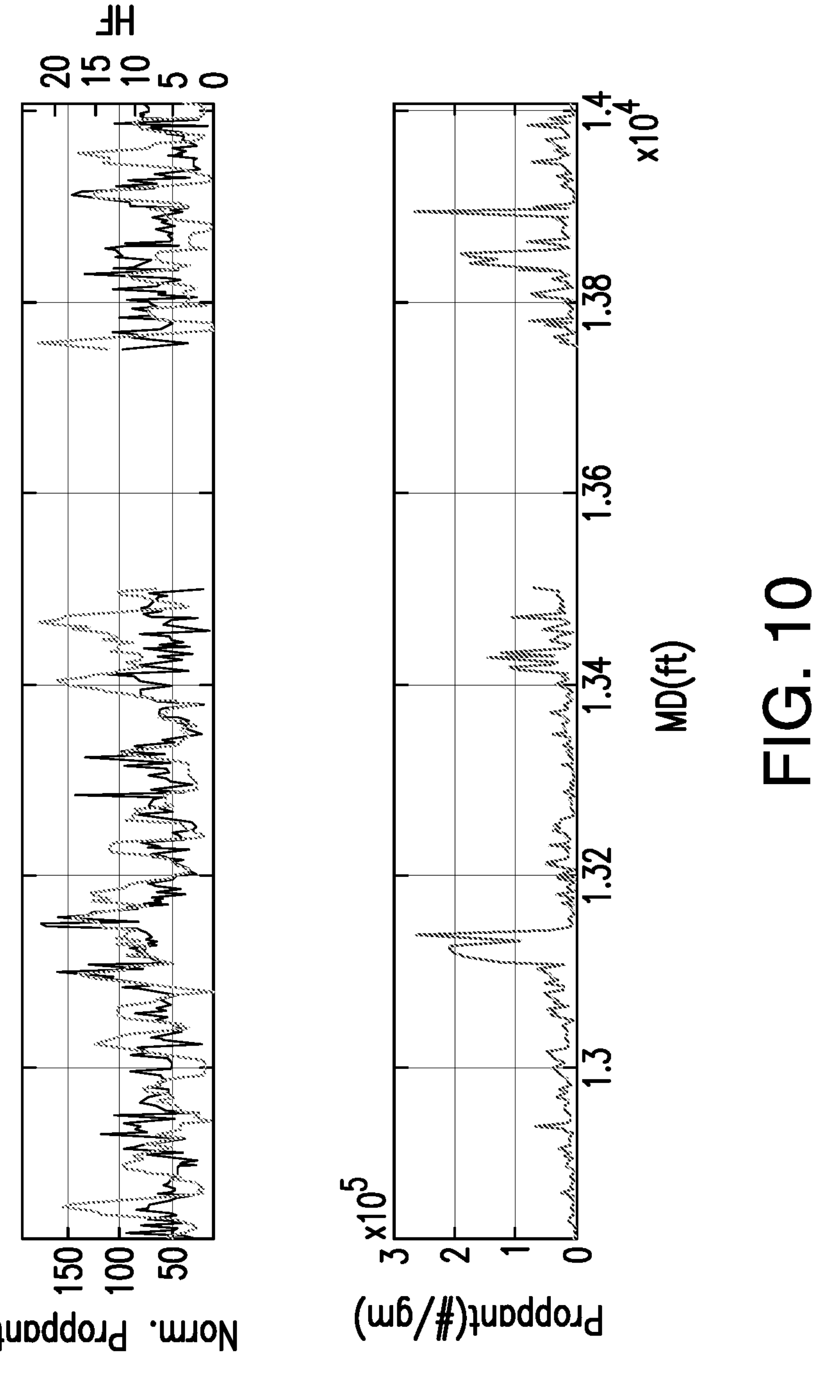
FIG. 10 shows a graphical representation of normalized proppant distribution and original proppant distribution according to one embodiment of the invention.

FIG. 10 shows a first normalized distribution curve as well as original proppant distribution before normalization. With normalization, proppant count drops at peaks. Convergence is shown between fracture data as well as pressure drop behavior. FIG. 10 shows a normalization parameter and how the parameter compares with the original proppant distribution. This normalization is preferably used when proppant sampling is at higher rates (for example, <1 sample every 6 feet).

Figure 11:
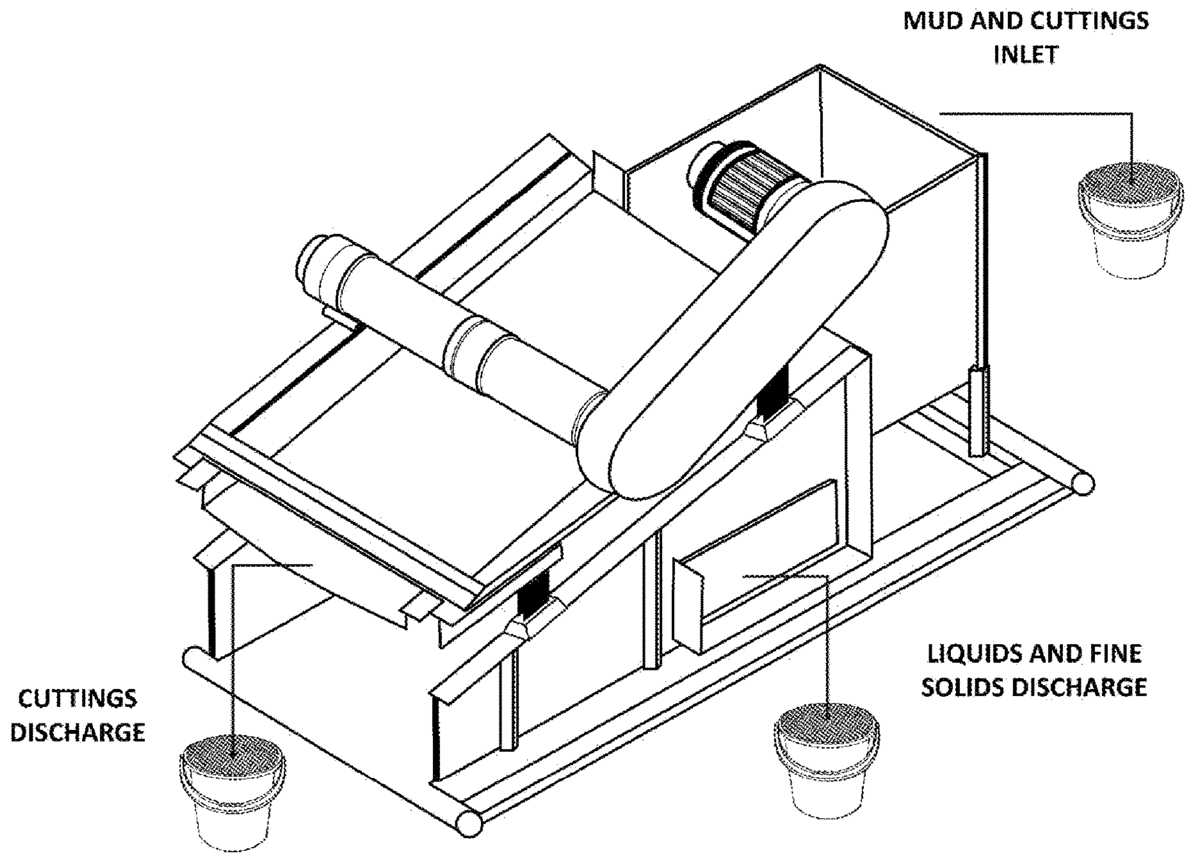
FIG. 11 shows a perspective view of a mud/drill cuttings handling system according to one embodiment of the invention.

FIG. 11 shows collection points located on a mud/drill cutting handling system 20 for a drilling rig. In order to take a proper composite sample at a wellsite that contains proppant (and other particles) and is representative of the length of the borehole drilled during the sampling period, a continuous liquid or solids slip stream collection can be used. A portion of a liquid mud return sample (that has not been filtered in any way) is redirected from the inlet 22, so as to only collect solids that settle at a bottom of a collection vessel. The collection vessel may be a bucket 30, such as shown in FIG. 11.

Another collection method includes collecting a slip stream of separated drill cuttings from a screen at a cuttings discharge location 24 and/or the liquid and fine solids discharge 26 of the mud handling system 20. This can be done by placing a bucket 30 under the falling cuttings at one location of the screen. The bucket 30 can have a fine screen 32 placed on top so as to prevent large cuttings from entering the bucket 30.

Figure 12:
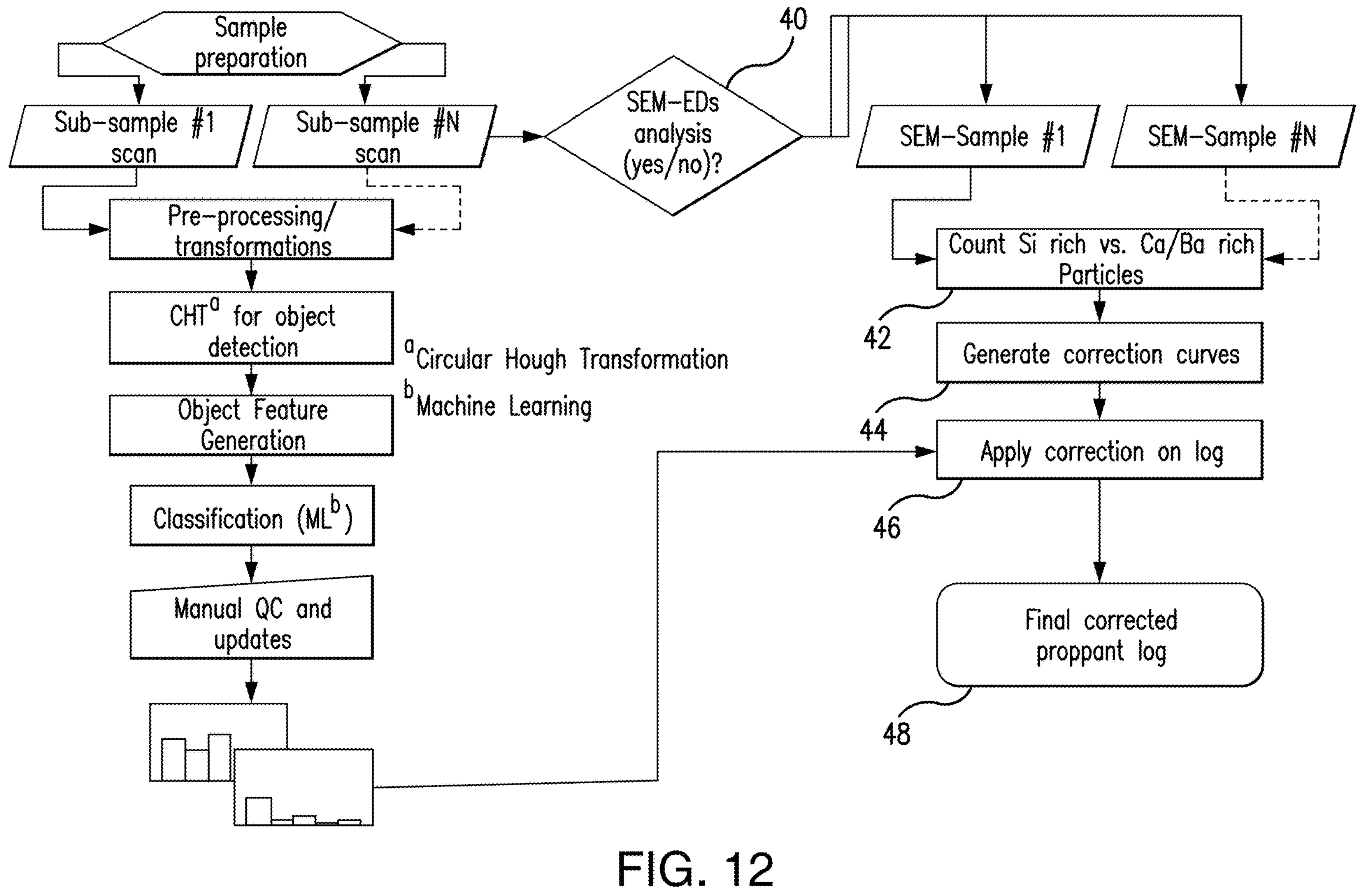
FIG. 12 shows a flow chart of a modified workflow with SEM analysis-based QC according to one embodiment of the invention.

FIG. 12 shows a modified workflow with SEM analysis-based quality control in a flowchart according to the invention. The flow chart details to obtain final corrected proppant log data from original sample preparation. The left side of the flow chart includes the steps of the imaging process. The right side of the flow chart includes the steps of the further analysis according to embodiments of this invention. As shown in FIG. 12, N-number of subset samples are sent for SEM analysis in step 40. In step 42, the silicon vs. calcium/barium particles are determined for each sample by the SEM. This analysis provides the correction factor, namely correction curves in step 44, which are applied for correction of the log data from the imaging process in step 46, resulting in the corrected proppant log 48.

In embodiments of this invention, the correction curve looks to compare a relative abundance of the proppant observed in the scanned samples (from image analysis) vs. the abundance of proppant from the SEM scans, where elemental classification is possible to get accurate proppant counts vs. other minerals such as calcites and sulphates. An $\alpha$ parameter ($\alpha$=number of proppant particles/number of other minerals with proppant-like optical characteristics, i.e., calcites, barite, etc.) is obtained. Then one can cross-plot values from the two analysis techniques and use regression fit to get a correction factor (slope/intercept). In order to identify all potential proppant-like particles, the elemental composition of baseline samples are studied (rock with no proppant), as well as various chemical additives used in the frac fluid.

Figure 13:
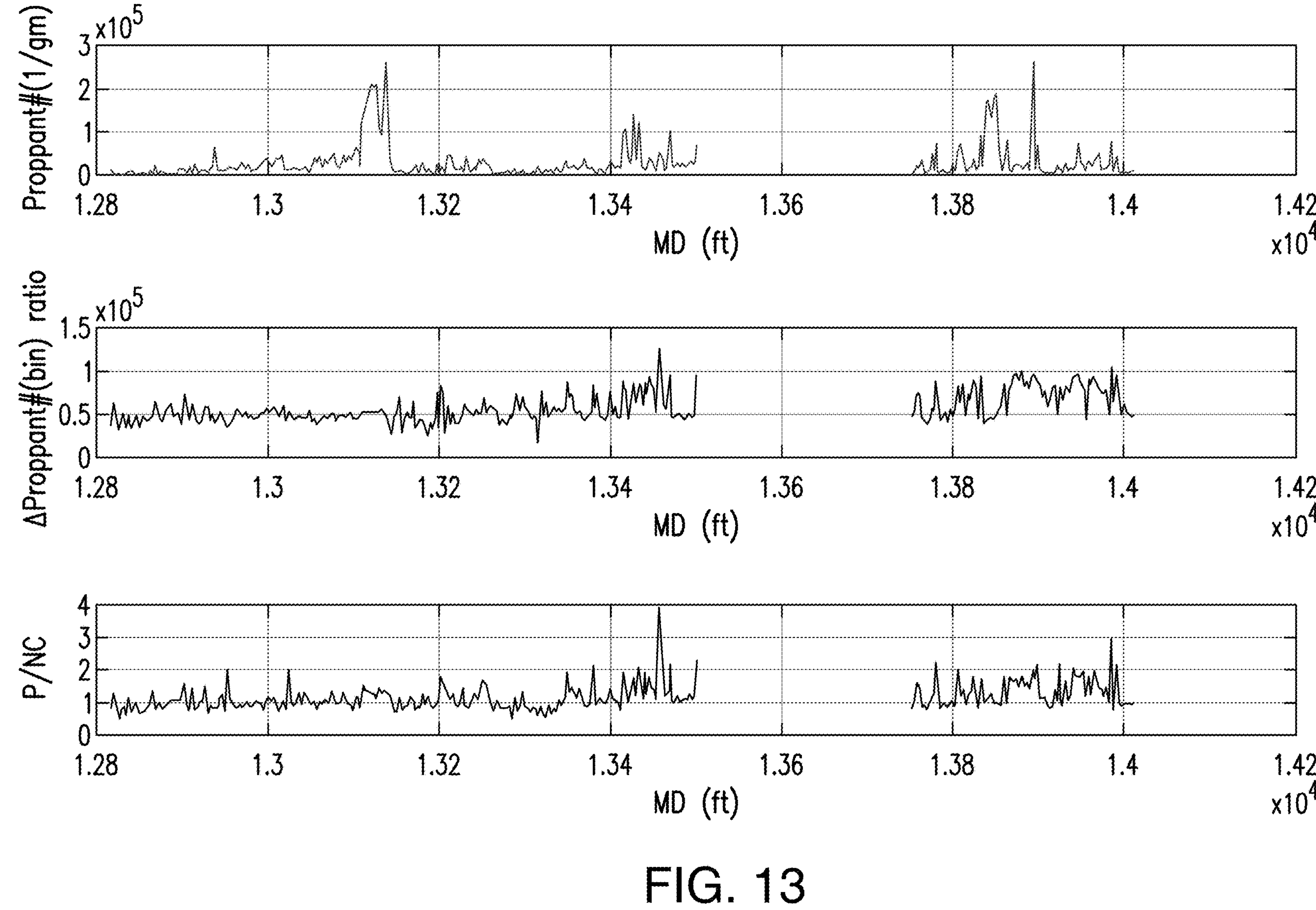
FIG. 13 shows a series of charts of plotted size distributions of proppant according to one embodiment of the invention.

FIG. 13 shows representations of extracting and plotting size distributions of proppant. FIG. 13 shows original proppant counts as well as proppant to calcite ratios and data relative to size distribution of proppant. The size distribution can be calculated as follows:

$$\Delta\text{Proppant\#(Bin)} = \frac{1-(\text{Count}_{100-125}-\text{count}_{125-150}-\text{Count}_{150-175})}{(\text{Count}_{100-125}+\text{count}_{125-150}+\text{Count}_{150-175})}$$

Figure 14:
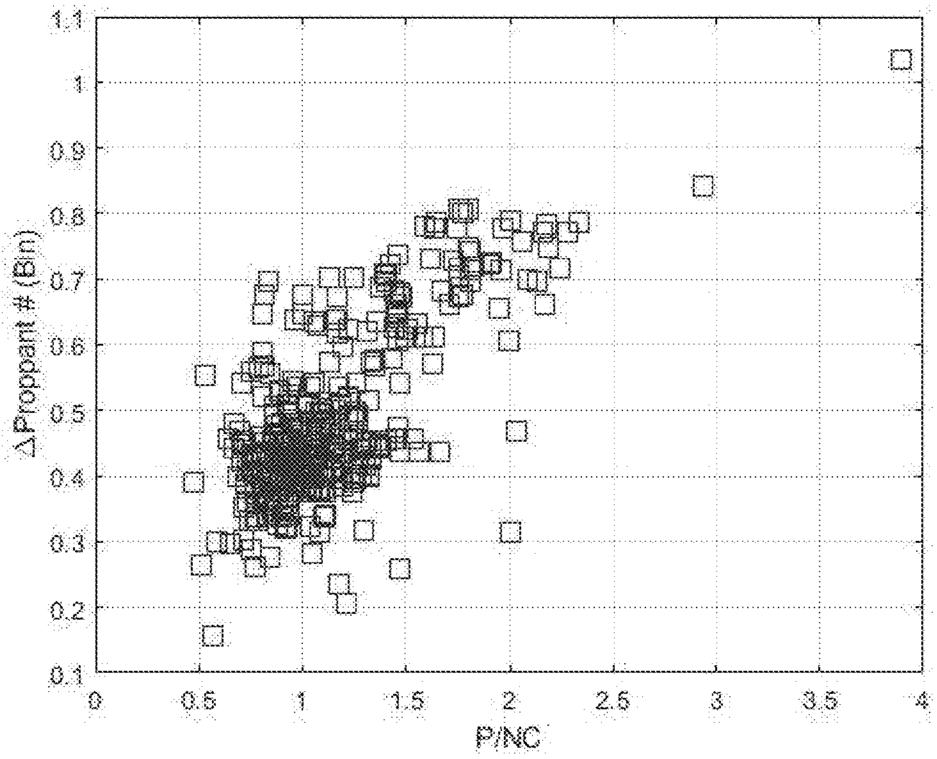
FIG. 14 shows a graphical representation of mesh proppant and normalized proppant distribution according to one embodiment of the invention.

Using values obtained from this calculation, various parameters can be found from proppant samples such as the size and quantity of proppant (with the ideal values being close to 100 microns of proppant). The concentration of the ideal 100 micron proppant is further shown in FIG. 14. FIG. 14 shows that having a majority of proppant particles in a higher level bin results in a higher likelihood of those particles being 100 micron mesh proppant particles.

Figure 15:
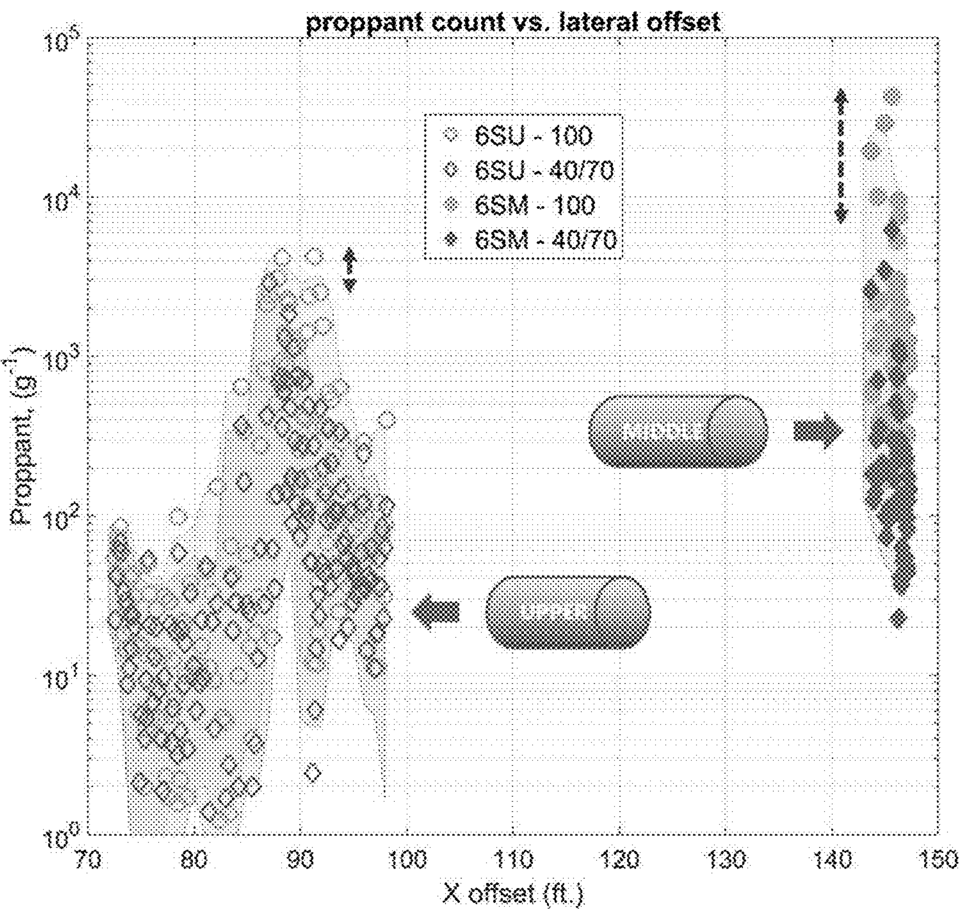
FIG. 15 shows a graphical representation of proppant count vs. lateral well offset.

In additional embodiments of this invention, the determined information and attributes of the samples is used to characterize proppant distribution. For example, consider the following β parameter:

$$\beta_i = SF \times \frac{C_{125-150} + C_{150-175}}{C_{100-125} + C_{125-150} + C_{150-175}}$$

where Ca-b indicates the number of proppant particles in a given size range [a, b], defined in microns. A higher β value indicates relatively more larger particles, whereas a smaller value indicates higher amounts of smaller particles at the sampled location. This is useful in interpreting a source of the observed proppant and/or associated hydraulic fractures at the sampled location. This is because proppant distribution is governed by vertical and lateral transport behavior which is a function of particle transport in suspended mediums. As an example, the impact of lateral transport distances can be seen in FIG. 15, where the upper Wolfcamp formation (WC) core has similar distributions of 100 mesh (smaller) and 40/70 (larger) mesh proppant (though 100 mesh is generally more compared to 40/70 mesh). On the other hand, the middle WC core shows significantly larger proportion of 100 mesh proppant compared to 40/70 mesh. The likely cause is the larger lateral offset of the sampled core location with the middle WC well (~150 ft) when compared to the upper WC well (~70 ft to 100 ft).

Figure 16:
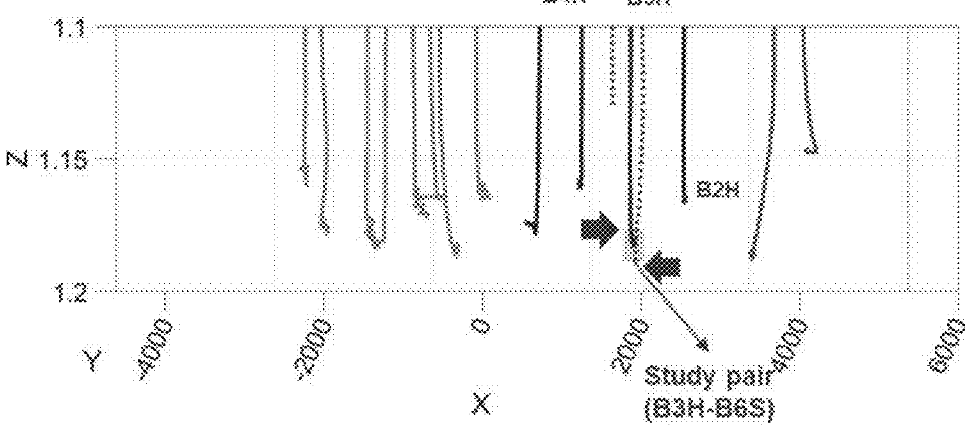
FIGS. 16 and 17 show an exemplary proppant log, and the cross-well interconnections between two example wells.
Figure 17:
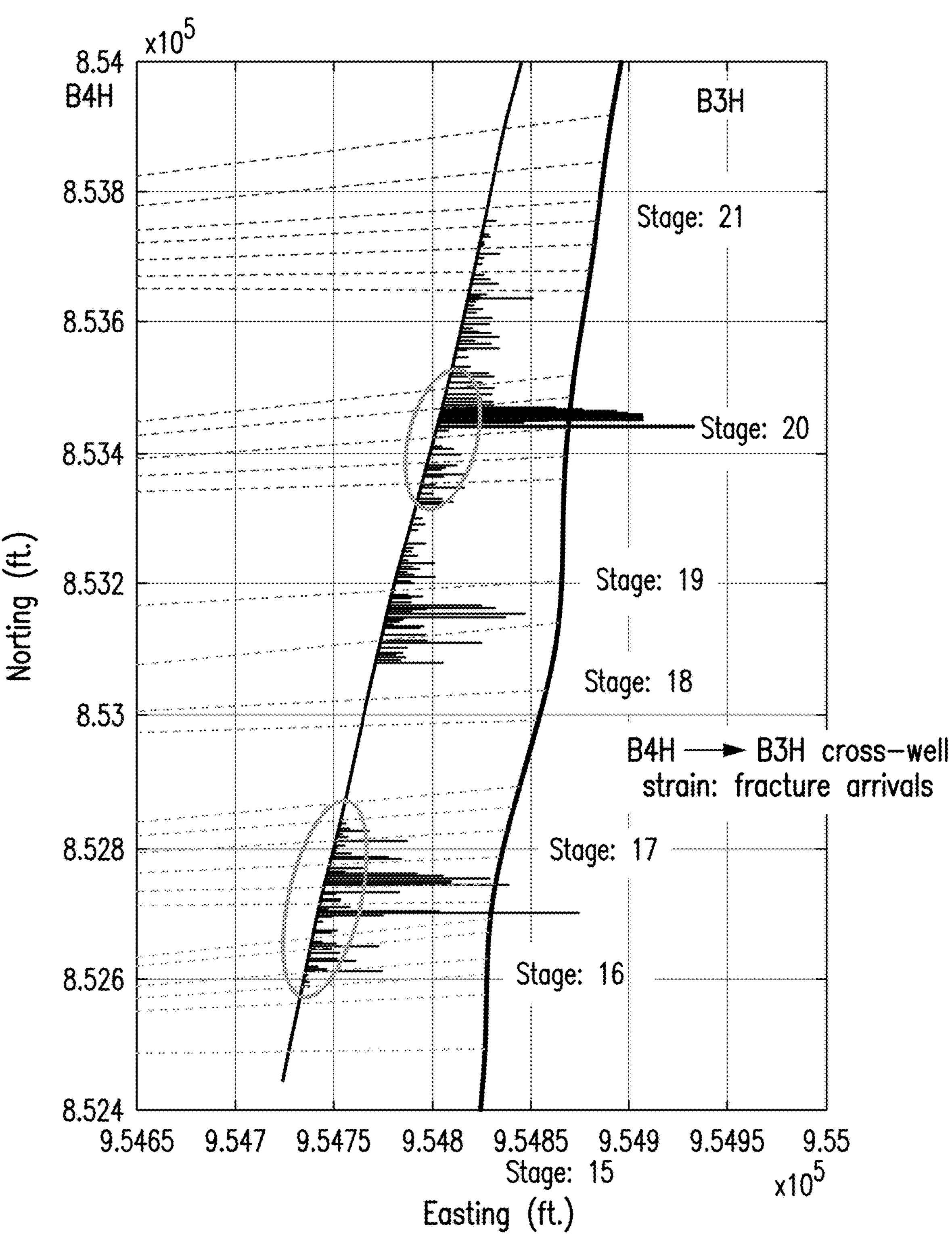

This template for interpretation has been verified in field tests where fracture propagation has been independently quantified using cross-well fiber (strain change) response. FIG. 16 highlights two sections along the proppant log where significant cross-cutting hydraulic fractures from a well farther afield (B4H) intersects the well that is being sampled (B3H). Thus, the expectation is that significant proppant observed across stage 20 (FIG. 17) are associated with B4H fractures and not B3H fractures.

Figure 18:
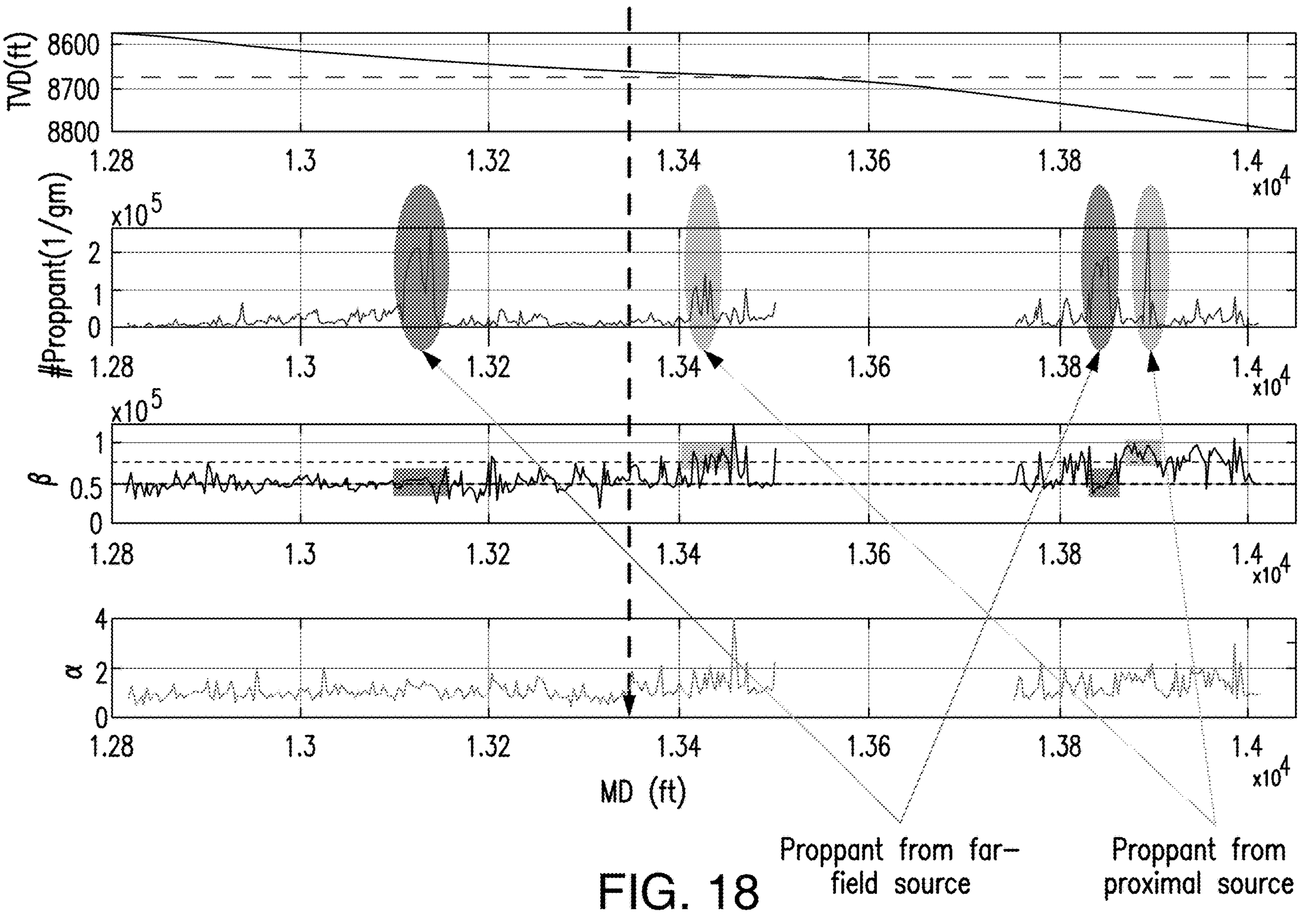
FIG. 18 shows another example proppant log to illustrate aspects of this invention.

To validate the understanding from cross-well fracture arrivals, the distribution of the β parameter from proppant log is looked at to make the interpretations. Referring to FIG. 18, note that the first peak at ~ 13100' corresponds to relatively smaller particles as per the β parameter, but later peaks such as at 13430' correspond with larger proppant particles. Thus the first section is likely associated with fractures from B4H and the second section with more proximal B3H well. This interpretation template can be applied more generally on any proppant log and is especially useful when there is good well control in the pad where this log is being run.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method for processing proppant from a well, the method comprising the steps of:

collecting a plurality of proppant samples during drilling of a well;

imaging the plurality of proppant samples collected to obtain baseline proppant values within the plurality of proppant samples;

analyzing a sample subset of the plurality of proppant samples to determine an elemental composition of the sample subset to distinguish proppant from other mineral particles in the sample subset, wherein the analyzing includes imaging the sample subset using an imaging technique that generates elemental composition information;

determining a correction factor from the elemental composition, wherein the correction factor is an element ratio of proppant to calcium and/or barium in the sample subset of the plurality of proppant samples; and applying the correction factor to the imaging results to correct the baseline proppant values.

2. The method of claim 1, further comprising:

determining the elemental composition with scanning electron microscopy (SEM) of the sample subset.

3. The method of claim 1, further comprising:

determining a distance zone within the well for the sample subset; and applying the correction factor to all proppant samples within the distance zone.

4. The method of claim 1, wherein the correction factor is a correction curve.

5. The method of claim 1, wherein the correction factor is an element ratio of silicon to calcium and/or barium in the sample subset of the plurality of proppant samples.

6. The method of claim 1, wherein applying the correction factor comprises adjusting an imaging element ratio in the imaging results as a function of the element ratio of the correction factor.

7. The method of claim 1, further comprising normalizing the correction factor as a function of a rate of drilling or penetration at a time of the sample collection.

8. The method of claim 1, further comprising:

determining a number of proppant particles in the sample subset within each of a plurality of particle size ranges; and interpreting hydraulic fractures as a function of a particle size distribution within the sample subset.

9. The method of claim 1, further comprising:

determining a source of proppant in the sample subset as a function of proppant particle size within the sample subset.

10. The method of claim 1, further comprising:

collecting the sample subset at one of a mud and cuttings inlet, a liquids and fine solids discharge, and/or a cuttings discharge of a hydraulic fracturing mud cleaner or shale shaker.

11. A method for processing proppant from a well, the method comprising the steps of:

collecting a plurality of proppant samples during drilling of a well;

imaging the plurality of proppant samples collected to obtain baseline proppant values within the plurality of proppant samples;

establishing proppant log data of the baseline proppant values;

analyzing at least a sample subset of the plurality of proppant samples by applying scanning electron microscopy (SEM) to the sample subset to obtain a SEM elemental composition analysis of the sample subset to distinguish proppant from other mineral particles in the sample subset;

generating a regression model correction factor by comparing the imaging results to the SEM elemental analysis; and validating or correcting the proppant log data with the regression model correction factor.

12. The method of claim 11, further comprising:

applying the correction factor to a proppant log; and producing a corrected proppant log.

13. The method of claim 11, further comprising:

determining a distance zone within the well for each of the proppant samples; and applying the correction factor to all proppant samples within the distance zone.

14. The method of claim 11, wherein the correction factor is an element ratio of silicon to calcium and/or barium in the at least a sample subset.

15. The method of claim 11, wherein applying the correction factor comprises adjusting an imaging element ratio in the imaging results as a function of the element ratio of the correction factor.

16. The method of claim 11, further comprising:

normalizing the correction factor as a function of a rate of drilling or penetration at a time of the sample collection.

17. The method of claim 11, further comprising:

determining a number of proppant particles in the at least a sample subset within each of a plurality of particle size ranges; and interpreting hydraulic fractures as a function of the particle size distribution within the at least a sample subset.

18. The method of claim 11, further comprising:

determining a source of proppant in the at least a sample subset as a function of proppant particle size within the at least a sample subset.

* * * * *